United States Patent [19]

Heald et al.

[11] 4,364,948

[45] Dec. 21, 1982

[54] PYRAZOLO[3,4-b]PYRIDINE COMPOUNDS

[75] Inventors: Anthony F. Heald, Glen Mills, Pa.; Richard A. Wildonger, Elmwood, Del.

[73] Assignee: ICI Americas Inc., Wilmington, Del.

[21] Appl. No.: 306,481

[22] Filed: Sep. 28, 1981

[51] Int. Cl.³ .................... A61K 31/44; C07D 471/04
[52] U.S. Cl. ................................... 424/256; 546/120
[58] Field of Search ........................ 546/120; 424/256

[56] References Cited

U.S. PATENT DOCUMENTS 3,755,340   8/1973   Hoehn et al. ...................... 546/120

OTHER PUBLICATIONS

Kripalani et al., Federation Proceedings, vol. 37, p. 271, (1978).

Primary Examiner—Henry R. Jiles
Assistant Examiner—Bernard Dentz
Attorney, Agent, or Firm—John M. Sheehan; David J. Levy

[57] ABSTRACT

Certain pyrazolo[3,4-b]pyridine compounds which are useful for their activity in the central nervous system of warm-blooded animals, of the following formula (I)

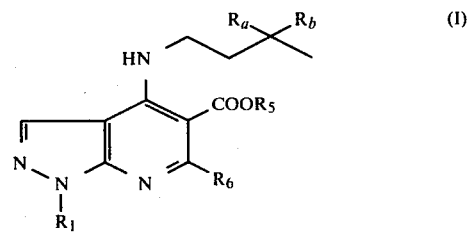

wherein
$R_1$ is lower alkyl;
$R_a$ is hydrogen and $R_b$ is hydroxy or $R_a$ and $R_b$ combine to form a =O group;
$R_5$ is hydrogen or lower alkyl; and
$R_6$ is lower alkyl, and the pharmaceutically-acceptable salts thereof.

11 Claims, No Drawings

PYRAZOLO[3,4-b]PYRIDINE COMPOUNDS

BACKGROUND OF THE INVENTION

Certain pyrazolo[3,4-b]pyridine compounds have been described in U.S. Pat. No. 3,755,340 issued Aug. 28, 1973, as being central nervous system (CNS) depressants. In particular, 4-butylamino-1-ethyl-1H-pyrazolo[3,4-b]pyridine-5-carboxylic acid ethyl ester is shown and has been given the generic name cartazolate. The study of the pharmacology of cartazolate has included investigation of the metabolites formed in monkeys after its administration. Urinary metabolites having gamma-hydroxylation of the 4-butylamino side chain have been reported in Federation Proceedings, Vol. 37, page 271 (1978). Further, Column 22 of U.S. Pat. No. 3,755,340 sets forth a synthesis of 4-n-butylamino-1-ethyl-6-methyl-1H-pyrazolo[3,4-b]pyridine-5-carboxylic acid ethyl ester which has the generic name tracazolate.

Some of the compounds of the invention are blood metabolites of tracazolate in rats which have been found themselves to possess significant pharmaceutical activity as modifiers of CNS activity, e.g. as anxiolytics.

SUMMARY OF THE INVENTION

Various 4-(substituted butylamino)-1-alkyl-6-alkyl-1H-pyrazolo[3,4-b]pyridine-5-carboxylic acid or alkyl ester compounds are described and shown to be useful as pharmaceuticals in the alteration of central nervous system activity. Particularly, compounds of the invention serve as anxiolytic agents.

DETAILED DESCRIPTION OF THE INVENTION

The present invention provides pyrazolopyridine compounds of the following formula (I):

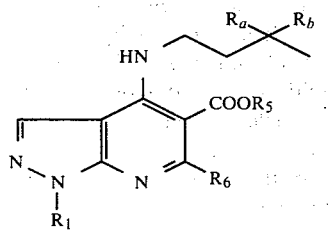

wherein $R_1$ is lower alkyl; $R_a$ is a hydrogen and $R_b$ is hydroxy or $R_a$ and $R_b$ combine to form a =O, or oxo, group; $R_5$ is hydrogen or lower alkyl; and $R_6$ is lower alkyl, and the pharmaceutically-acceptable salts thereof.

$R_1$ may more particularly be branched or straight chain lower alkyl, e.g. of about 1 to 4 carbon atoms. A specific alkyl group for $R_1$ is ethyl.

$R_5$ may more particularly be branched or straight chain lower alkyl, e.g. of about 1 to 4 carbon atoms. A specific alkyl group for $R_5$ is ethyl.

$R_6$ may more particularly be branched or straight chain lower alkyl, e.g. of about 1 to 4 carbon atoms. A specific alkyl group for $R_6$ is methyl.

Specific compounds of the invention include those wherein $R_1$ is ethyl; $R_a$ is hydrogen; $R_b$ is hydroxy; $R_5$ is ethyl; and $R_6$ is methyl or wherein $R_1$ is ethyl; $R_a$ and $R_b$ combine to form a =O group; $R_5$ is ethyl; and $R_6$ is methyl.

It is to be understood that various compounds within the scope of formula (I) exist in the form of optical isomers as is known in the art and the present invention includes all such isomers. For example, when $R_a$ is hydrogen and $R_b$ is hydroxy, the carbon atom to which they are attached would be considered asymmetric and the present invention includes both isomers which could be formed based in this asymmetry.

The pharmaceutically acceptable salts of the invention include acid-addition salts when $R_5$ is lower alkyl and base-addition salts when $R_5$ is a hydrogen atom. Examples of suitable salts include non-toxic, physiologically acceptable acid-addition salts such as mineral acid salts, e.g. hydrohalides, especially hydrochlorides and hydrobromides, sulfates, nitrates, and phosphates. Examples of base-addition salts include alkali or alkaline earth metal salts such as sodium and potassium.

The compounds of the invention may be prepared by routes analogous to those described in U.S. Pat. No. 3,755,340 and more specifically as follows. An aminopyrazole of the following formula (II):

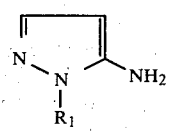

is prepared by ring closure of an aldehyde hydrazone of the formula $N\equiv CCH_2CH_2NHN=CHR_{10}$, wherein $R_{10}$ is hydrogen or lower alkyl as described in U.S. Pat. No. 3,755,340. The compound of formula (II) then is reacted, e.g. at a temperature of about 110° to 130° C. in the presence of poly-phosphoric acid, with an alkylcarbonyl malonic acid diester of the following formula (III):

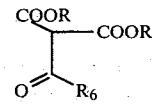

Compounds of the formula (III) are known, e.g. acetomalonic acid diethyl ester, and may be prepared by the reaction of an alkane acid chloride, e.g. acetyl chloride, with the anion of a dialkyl ester of malonic acid. The reaction product of a compound of the formulae (II) and (III) is an intermediate of the following formula (IV):

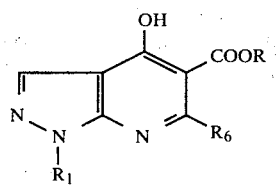

wherein R is alkyl such as lower alkyl, e.g. ethyl, and $R_1$ and $R_6$ are lower alkyl. To yield the desired $R_5$ grouping in formula (I), the —COOR moiety in (IV) may either be transesterified as is known in the art with a lower alkyl alcohol or saponified to yield a compounds of formula (I) with $R_5$=H by reaction with an alkali hydroxide such as sodium or potassium hydroxide. These reactions may be carried out at this stage or after placement of the butylamino group although saponification, if $R_5$=H is desired, should preferably be carried out after placement of the butylamino. Compounds of formula (IV) may then be converted to a halo compound of the following formula (V):

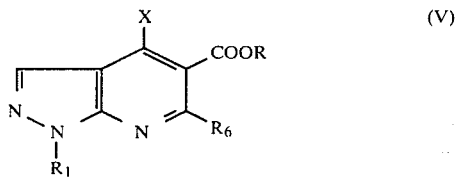

wherein X is chloro or bromo by reaction of (IV) with a chlorinating or brominating agent such as phosphorus oxychloride. For compounds of formula (I) wherein $R_a$ and $R_b$ combine to form =O, the corresponding compound of formula (V), X=chloro or bromo, may then be reacted with 3-oxo-n-butylamine of the formula $H_2NCH_2CH_2COCH_3$. The keto group of the 3-oxo-n-butylamine may have to be protected prior to the reaction, e.g. by use of the corresponding ketal. For compounds of formula (I) wherein $R_a$ is hydrogen and $R_b$ is hydroxy, the corresponding compound of the formula (V), X=chloro or bromo, is reacted with 3-hydroxy-n-butylamine of the formula $H_2NCH_2CH_2CHOHCH_3$. Alternatively, the corresponding compound of formula (V), X=chloro or bromo, is first reacted with ammonia to give a compound of formula (V), X=$NH_2$, which is then reacted with 1-halo-3-hydroxy-n-butane; e.g. 1-bromo- or 1-chloro-3-hydroxy-n-butane.

Starting materials of formula (III) may be prepared by methods generally described in Organic Synthesis, Coll. Vol. IV pages 285–288 (1963).

3-oxo-n-butylamine and its ketal may be prepared by the process of reacting phthalimide with methyl vinyl ketone to give N-(3-oxo-n-butyl)phthalimide which is then reacted with ethylene glycol to yield the corresponding ketal. The ketal is then reacted with hydrazine to remove the phthalic acid moiety and yield the ketal of 3-oxo-n-butylamine. Reaction of the ketal with dilute hydrochloric acid yields the HCl salt of 3-oxo-n-butylamine and the free amine can be obtained by basification with sodium bicarbonate.

3-hydroxy-n-butylamine may be prepared by first reacting 1-chloro-2-propanol with potassium cyanide to yield 3-hydroxybutyronitrile which is then hydrogenated with Raney nickel to give 3-hydroxy-n-butylamine.

The pharmaceutical compositions of the invention may be prepared and used according to methods known for the compounds cartazolate and tracazolate. Specifically, the new compounds of this invention are central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula (I), or non-toxic physiologically acceptable acid, if $R_5$=alkyl, or base, if $R_5$=H, addition salt thereof, may be administered orally or parenterally in a conventional dosage form such as tablet, pill, capsule, injectable or the like. A single dose, or preferably 2 to 4 divided daily doses, provided on a basis of about 1 to 50 mg per kilogram of body weight per day, preferably about 2 to 15 mg per kilogram per day, is appropriate. These may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice e.g. as described in U.S. Pat. No. 3,755,340.

Compounds of the invention have been shown to suppress CNS activity in warm blooded animals and particularly to suppress anxiety. Among the tests conducted to demonstrate the anxiolytic activity of the present compounds was the Shock-Induced Suppression of Drinking (Rats) (SSD) Test which was carried out as follows:

Male rats in the weight range of 200 to 220 grams are water-deprived for 48 hours and food-deprived for 24 hours before testing. Normally, the rats are orally intubated (5 ml/kg) with the test compound (based on mg/kg body weight). The vehicle control group of rats is also intubated by mouth. A positive control group of rats is also orally administered a control dose of 18 mg/kg of chlordiazepoxide. Randomization is utilized in dosing. The rats are returned to the cage for one hour. Sixty minutes after drug administration, the rat is quietly removed from its cage and the hind feet wiped with Signa electrode gel made by Parker Laboratories of Orange, N.J. When intraperitoneal (i.p.) administration was used, the protocol was identical except that the drugs were administered (5 ml/kg) 30 minutes prior to testing. The rat is placed on the floor in the chamber facing the licking tube. The animal is allowed 5 minutes to make 20 licking responses and receive the first shock (0.5 mA). If this does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to both the mean shocks of the vehicle and positive control groups via a Students' t-test. The higher the number of shocks received the higher the anti-conflict or anti-anxiety activity of the compound.

In the SSD test, the compound of the invention of formula (I) wherein $R_1$ is ethyl; $R_a$ is hydrogen; $R_b$ is hydroxy; $R_5$ is ethyl; and $R_6$ is methyl showed activity at 20 mg/kg i.p. indicated by a significant (less than 0.05, Students' t-test) increase in the number of shocks taken. Further, the compound of the invention of formula (I) wherein $R_1$ is ethyl; $R_a$ and $R_b$ combine to form a =O group; $R_5$ is ethyl; and $R_6$ is methyl showed activity at 40 mg/kg per os as determined by a significant (less than 0.05, Students' t-test) increase in the number of shocks taken.

Synthesis of compounds of the invention is demonstrated by the following Examples, degrees being in Centigrade (C) and the following abbreviations being used: mg (milligrams), kg (kilograms), g (grams), psi (pounds per square inch pressure), mMole (millimole), ml (milliliters) and mp (melting point). Conventional chemical abbreviations for the elements, e.g., C, H, N, and O, are also used.

EXAMPLE 1 a. 1-Ethyl-6-methyl-4-hydroxy-1H-pyrazolo[3,4-b]pyridine-5-carboxylic acid ethyl ester 51.1 g of 1-ethyl-5-aminopyrazole (0.46 mole) and 101 g of acetomalonic acid ethyl ester (0.5 mole) are added to 224 g of polyphosphoric acid. The mixture is heated with stirring at 120° for three hours. After this period, the mixture is cooled, diluted with 1,000 ml of water and subsequently extracted twice with 300 ml portions of chloroform. The chloroform layers are collected, dried over sodium sulfate and the solvent is distilled off. Recrystallization of the residue (67 g) with petroleum ether yields 1-ethyl-6-methyl-4-hydroxy-1H-pyrazolo-[3,4-b]pyridine-5-carboxylic acid ethyl ester, mp 118°-120° C.

b. 4-Chloro-1-ethyl-6-methyl-1H-pyrazolo[3,4-b]pyridine-5-carboxylic acid ethyl ester A mixture of 49.1 g of 1-ethyl-6-methyl-4-hydroxy-1H-pyrazolo[3,4-b]pyridine-5-carboxylic acid ethyl ester (0.197 mole) and 250 ml of phosphorus oxychloride is refluxed for 4 hours. Then the excess phosphorus oxychloride is removed by vacuum distillation and the residue is treated with water. The 4-chloro compound (42 g) is filtered under suction and recrystallized from n-hexane, mp 54°-56° C.

c. 3-Hydroxy butyronitrile

A mixture of 109.15 g of 1-chloro-2-hydroxypropane (1.15 mole), 109.2 g of KCN (1.68 mole), and 16.4 g (0.086 mole) of KI in 600 ml of a mixture of 5:1 by volume ethanol:water were heated under reflux for 10 hours then cooled to room temperature and filtered. The filtrate was concentrated in vacuo and extracted with 4 washings of 200 ml of diethyl ether each. The combined extracts were dried over $MgSO_4$ and concentrated in vacuo to yield 62.7 g of crude product. The product was flash distilled to yield 45.1 g of product.

d. 3-Hydroxy-n-butylamine

A mixture of 25.04 g of 3-hydroxy butyronitrile (0.294 mole) in 300 ml of ammonia-saturated methanol was hydrogenated at 50 psi over 25 g of Raney Nickel with $H_2$ at room temperature for 7 hours. Catalyst was removed by filtration and the filtrate was concentrated in vacuo to yield 26.3 g of crude product which was partially purified by flash distillation to give 20.84 g (80% yield) of product.

e. 1-Ethyl-4-(3-hydroxy-n-butylamino)-6-methyl-1H-pyrazolo-[3,4-b]pyridine-5-carboxylic acid ethyl ester 2.75 each of 4-chloro-1-ethyl-6-methyl-1H-pyrazolo[3,4-b]pyridine-5-carboxylic acid ethyl ester and 3-hydroxy-n-butylamine are combined with 15.6 ml of dry toluene under $N_2$ and heated at 45° C. for 48 hours. The mixture was cooled to room temperature and the toluene layer was decanted from the oil that separated out. The toluene layer was washed with water and then dried and concentrated in vacuo to yield 3.7 g of product which crystallized on trituration with hexane. This was recrytallized from hexane to yield 1.91 g of white product mp 94.5°-96.5° C.

EXAMPLE 2 a. 3-Oxo-n-butylamine ketal

1. A mixture of 18 g (0.122 mole) of phthalimide, 8.7 g (0.12 mole) of methyl vinyl ketone and 70 ml of ethyl acetate is prepared. To this is added 3 ml of trimethyl benzyl ammonium hydroxide catalyst and the mixture was heated under reflux for ½ hour. The mixture was concentrated in vacuo to yield 37 g of tan solid product. The product was recrystallized from ethanol to yield 23.01 g of product mp 107°-111° C.

2. A mixture of 22.9 g (0.105 mole) N-(3-oxo-n-butyl)phthalimide, 9.95 g (0.160 mole) of ethylene glycol, and 0.3 g of para-toluene sulfonic acid in 450 ml of dry toluene under nitrogen atmosphere was heated under reflux for three hours while water was continuously removed. The mixture was cooled to room temperature and washed successively with an aqueous 5% $Na_2CO_3$ solution and water. The organic phase was dried and concentrated to yield 26.9 g of product mp 118°-122° C.

3. A mixture of 15 g (57.4 mMole) of N(3-oxo-n-butyl)phthalimide ketal and 3 g (60 mMole) of hydrazine hydrate in 250 ml $H_2O$ was heated under reflux for 1 hour then stirred overnight at room temperature. The mixture was treated with 2.4 g (60.3 mMole) of NaOH in 75 ml of water and continuously extracted with 750 ml of diethyl ether for 72 hours. The ether was tested for peroxide formation, then dried and concentrated in vacuo. The product was flash distilled to yield 3-oxo-n-butylamine ketal.

b. 1-Ethyl-6-methyl-4-(3-oxo-n-butylamino)-1H-pyrazolo[3,4-b]pyridine-5-carboxylic acid ethyl ester ketal A mixture of 0.25 g (0.93 mMole) of 1-ethyl-6-methyl-4-chloro-1H-pyrazolo[3,4-b]pyridine-5-carboxylic acid ethyl ester, 0.13 g (0.99 mMole) of 3-oxo-n-butyl amine ketal and 0.12 g (1.2 mMole) of triethyl amine in 1.5 ml of toluene was heated at 60° C. for 4 hours after which an additional equivalent (0.93 mMole) of triethyl amine was added. The mixture was further heated at 60° C. for additional 12 hours. The top layer was decanted off, washed with a 2% $NaHCO_3$ aqueous solution, dried and concentrated to yield 0.38 g of product which crystallized on standing. The product was recrystallized from hexane to yield 0.26 g of 1-ethyl-6-methyl-4-(3-oxo-n-butylamino)-1H-pyrazolo-[3,4-b]pyridine-5-carboxylic acid ethyl ester ketal mp 69°-72° C.

c. 1-Ethyl-6-methyl-4-(3-oxo-n-butylamino)-1H-pyrazolo-[3,4-b]pyridine-5-carboxylic acid ethyl ester A mixture of 3.65 g of 1-ethyl-6-methyl-4-(3-oxo-n-butylamino)-1H-pyrazolo[3,4-b]pyridine-5-carboxylic acid ethyl ester ketal in 45 ml of tetrahydrofuran and 22 ml of a 10% HCl aqueous solution was stirred overnight at room temperature. The mixture was basified with a 20% $NaHCO_3$ aqueous solution and extracted with ether. The ethereal phase was dried and then concentrated to yield 3.2 g of a white solid product which was recrystallized from hexane to yield 3.09 g of the ethyl ester of 1-ethyl-6-methyl-4-(3-oxo-n-butylamino)-1H-pyrazolo-[3,4-b]pyridine-5-carboxylic acid mp 84.5°-86.5° C.

What is claimed is:

1. A pyrazolopyridine compound of the following formula (I)

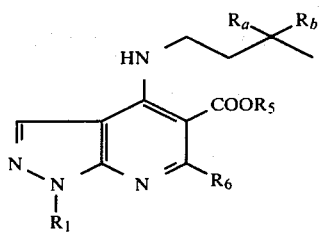

wherein
  $R_1$ is lower alkyl;
  $R_a$ is hydrogen and $R_b$ is hydroxy or $R_a$ and $R_b$ combine to form a $=O$ group;
  $R_5$ is hydrogen or lower alkyl; and
  $R_6$ is lower alkyl,
and the pharmaceutically-acceptable salts thereof.

2. The pyrazolopyridine of claim 1, wherein $R_1$ is ethyl.

3. The pyrazolopyridine of claim 1, wherein $R_a$ is hydrogen and $R_b$ is hydroxy.

4. The pyrazolopyridine of claim 1, wherein $R_a$ and $R_b$ combine to form a $=O$ group.

5. The pyrazolopyridine of claim 1, wherein $R_5$ is ethyl.

6. The pyrazolopyridine of claim 1, wherein $R_6$ is methyl.

7. The pyrazolopyridine of claim 1, wherein
  $R_1$ is ethyl;
  $R_a$ is hydrogen and $R_b$ is hydroxy;
  $R_5$ is ethyl; and
  $R_6$ is methyl.

8. The pyrazolopyridine of claim 1, wherein
  $R_1$ is ethyl;
  $R_a$ and $R_b$ combine to form a $=O$ group;
  $R_5$ is ethyl; and
  $R_6$ is methyl.

9. A pharmaceutical composition comprising an anxiolytically-effective amount of a pyrazolopyridine of claim 1 in association with a pharmaceutically-acceptable diluent or carrier.

10. A method of suppressing anxiety in a warm blooded animal comprising administering to a warm-blooded animal in need thereof a pharmaceutically effective amount of the composition of claim 9.

11. The pyrazolopyridine of claim 1, wherein said pharmaceutically-acceptable salts are selected from the group consisting of a hydrochloride, hydrobromide, sulfate, nitrate and phosphate.

* * * * *